United States Patent
Ahn et al.

(10) Patent No.: US 10,381,685 B2
(45) Date of Patent: Aug. 13, 2019

(54) LIQUID ELECTROLYTE ADDITIVE FOR LITHIUM SECONDARY BATTERY, NON-AQUEOUS LIQUID ELECTROLYTE AND LITHIUM SECONDARY BATTERY COMPRISING THE SAME

(71) Applicant: LG Chem, Ltd., Seoul (KR)

(72) Inventors: Kyoung Ho Ahn, Daejeon (KR); Sol Ji Park, Daejeon (KR); Chul Haeng Lee, Daejeon (KR); Jeong Woo Oh, Daejeon (KR)

(73) Assignee: LG Chem, Ltd. (KR)

( * ) Notice: Subject to any disclaimer, the term of this patent is extended or adjusted under 35 U.S.C. 154(b) by 93 days.

(21) Appl. No.: 15/516,106

(22) PCT Filed: Oct. 1, 2015

(86) PCT No.: PCT/KR2015/010415
§ 371 (c)(1),
(2) Date: Mar. 31, 2017

(87) PCT Pub. No.: WO2016/053040
PCT Pub. Date: Apr. 7, 2016

(65) Prior Publication Data
US 2017/0294682 A1    Oct. 12, 2017

(30) Foreign Application Priority Data

Oct. 2, 2014  (KR) .......... 10-2014-0133432
Oct. 1, 2015  (KR) .......... 10-2015-0138640

(51) Int. Cl.
| | |
|---|---|
| *H01M 10/052* | (2010.01) |
| *H01M 10/0567* | (2010.01) |
| *C07C 265/02* | (2006.01) |
| *C07C 265/10* | (2006.01) |
| *C07C 265/12* | (2006.01) |
| *H01M 10/0525* | (2010.01) |
| *H01M 10/0569* | (2010.01) |

(52) U.S. Cl.
CPC ....... *H01M 10/0567* (2013.01); *C07C 265/02* (2013.01); *C07C 265/10* (2013.01); *C07C 265/12* (2013.01); *H01M 10/052* (2013.01); *H01M 10/0525* (2013.01); *H01M 10/0569* (2013.01)

(58) Field of Classification Search
CPC ............ H01M 10/052; H01M 10/0525
See application file for complete search history.

(56) References Cited

U.S. PATENT DOCUMENTS

| | | |
|---|---|---|
| 2007/0059588 A1 | 3/2007 | Lee et al. |
| 2013/0059210 A1* | 3/2013 | Yu .............. H01M 4/13 429/338 |
| 2013/0216919 A1 | 8/2013 | Tokuda et al. |
| 2013/0330609 A1 | 12/2013 | Sawa et al. |
| 2015/0155106 A1 | 6/2015 | Takada et al. |
| 2016/0006076 A1 | 1/2016 | Kim et al. |
| 2016/0013517 A1 | 1/2016 | Nakazawa et al. |

FOREIGN PATENT DOCUMENTS

| | | |
|---|---|---|
| JP | 2012182130 A | 9/2012 |
| JP | 2012227060 A | 11/2012 |
| JP | 2013206708 A | 10/2013 |
| KR | 20070031807 A | 3/2007 |
| KR | 20130108286 A | 10/2013 |
| KR | 20140036156 A | 3/2014 |
| WO | 2014006845 A1 | 1/2014 |
| WO | 2014157591 A1 | 10/2014 |

OTHER PUBLICATIONS

Extended European Search Report for Application No. 15846320.8 dated Jun. 8, 2017, 3 pages.
International Search Report From PCT/KR2015/010415 dated Nov. 25, 2015.

* cited by examiner

*Primary Examiner* — Olatunji A Godo
(74) *Attorney, Agent, or Firm* — Lerner, David, Littenberg, Krumholz & Mentlik, LLP

(57) ABSTRACT

The present disclosure provides a non-aqueous liquid electrolyte comprising a non-aqueous organic solvent, a lithium salt, and an additive that is an isocyanate-based compound comprising a carbon-carbon triple bond.
By comprising the isocyanate-based compound additive comprising a carbon-carbon triple bond of the present disclosure in the non-aqueous liquid electrolyte, lifespan properties and high temperature durability are capable of being enhanced, and internal resistance of a battery is capable of being reduced.

16 Claims, 1 Drawing Sheet

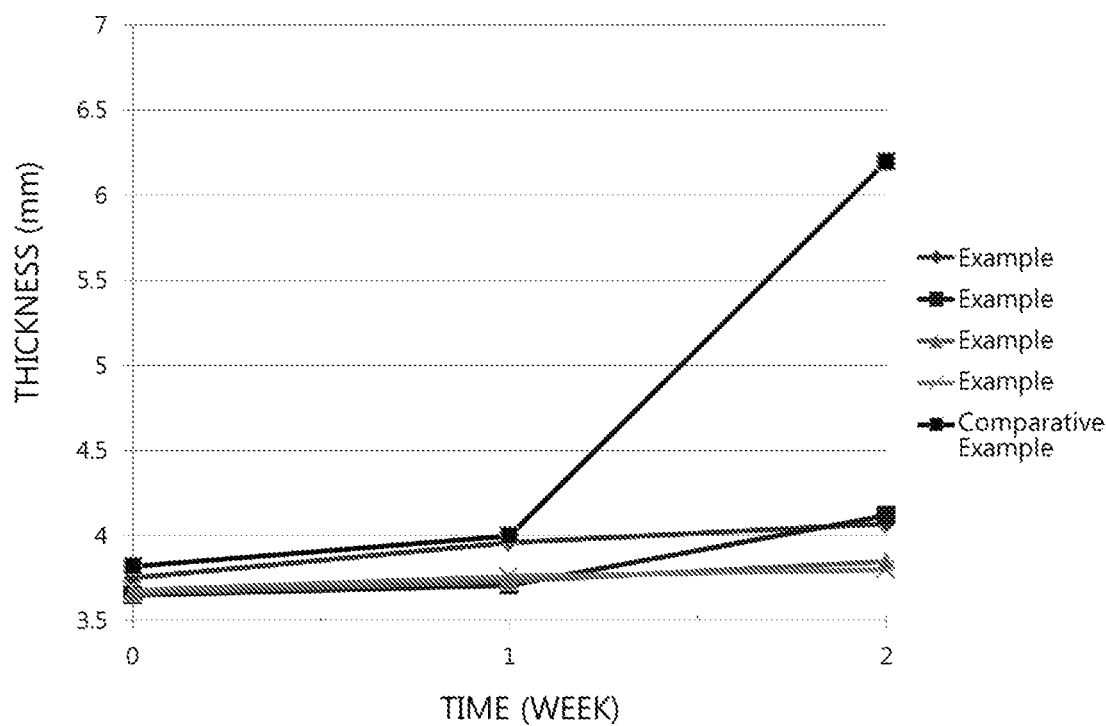

LIQUID ELECTROLYTE ADDITIVE FOR LITHIUM SECONDARY BATTERY, NON-AQUEOUS LIQUID ELECTROLYTE AND LITHIUM SECONDARY BATTERY COMPRISING THE SAME

CROSS-REFERENCE TO RELATED APPLICATIONS

This application is a national phase entry under 35 U.S.C. § 371 of International Application No. PCT/KR2015/010415, filed Oct. 1, 2015, which claims priority to Korean Patent Application No. 10-2014-0133432, filed Oct. 2, 2014 and Korean Patent Application No. 10-2015-0138640, filed Oct. 1, 2015, the disclosures of which are incorporated herein by reference.

Technical Field

The present disclosure relates to a secondary battery having enhanced lifespan properties and high temperature durability by comprising a non-aqueous liquid electrolyte that comprises an isocyanate-based compound in the secondary battery.

Description of the Related Art

With increases in technology developments and demands for mobile devices, demands for secondary batteries as an energy source have rapidly increased, and among such secondary batteries, lithium secondary batteries having high energy density and voltage have been commercialized and widely used.

As a positive electrode active material of a lithium secondary battery, lithium metal oxides have been used, and as a negative electrode active material, lithium metal, lithium alloys, crystalline or amorphous carbon or carbon complexes have been used. A secondary battery is manufactured by applying the active material on a collector to proper thickness and length or applying the active material itself in a film form, and winding or laminating the result with a separator, an insulator, to form an electrode group, then placing the result in a can or a container similar thereto, and then injecting a liquid electrolyte thereto.

Such a lithium secondary battery experiences charge and discharge while repeating intercalation and deintercalation of lithium ions from a lithium metal oxide of a positive electrode to a graphite electrode of a negative electrode. Herein, the lithium reacts with a carbon electrode due to high reactivity, and forms a film on the negative electrode surface by producing $Li_2CO_3$, LiO, LiOH and the like. Such a film is referred to as a solid electrolyte interface (SEI) film, and the SEI film formed at the beginning of charge prevents a reaction of lithium ions with a carbon negative electrode or other materials while charging and discharging. In addition, the SEI film performs a role of an ion tunnel and passes only lithium ions. This ion tunnel solvates lithium ions and performs a role of preventing the collapse of the carbon negative electrode structure by high molecular weight organic solvent of a liquid electrolyte moving together being co-intercalated to the carbon negative electrode.

Accordingly, a solid SEI film needs to be formed on a negative electrode of a lithium secondary battery in order to enhance a high temperature cycle and a low temperature power output of the lithium secondary battery. Once the SEI film is formed at the initial charge, the film prevents a reaction of lithium ions with a negative electrode or other materials when repeating charge and discharge by battery use thereafter, and performs a role of an ion tunnel between a liquid electrolyte and the negative electrode passing only lithium ions.

In existing technologies, battery lifespan enhancement has been difficult to be expected in a liquid electrolyte that does not comprise a liquid electrolyte additive or comprises a liquid electrolyte additive having poor properties due to the formation of a non-uniform SEI film. Moreover, even when a liquid electrode additive is comprised but the amounts of the additive to be added are not adjusted to required amounts, there has been a problem in that a positive electrode surface is decomposed in a high temperature reaction due to the liquid electrolyte additive, or the liquid electrolyte causes an oxidation reaction and ultimately, irreversible capacity of a secondary battery increases and durability of a battery declines.

DISCLOSURE OF THE INVENTION

Technical Problem

The present disclosure has been made in view of the above. The inventors of the present application have identified that power output properties and stability are enhanced when comprising an isocyanate-based compound additive that comprises a carbon-carbon triple bond in a non-aqueous liquid electrolyte, and have completed the present disclosure.

Technical Solution

One embodiment of the present disclosure provides a non-aqueous liquid electrolyte comprising a non-aqueous organic solvent, a lithium salt and an additive, wherein the additive is an isocyanate-based compound comprising a carbon-carbon triple bond.

The isocyanate-based compound comprising a carbon-carbon triple bond may comprise one or more compounds selected from the group consisting of compounds represented by the following Chemical Formulae 1 to 3.

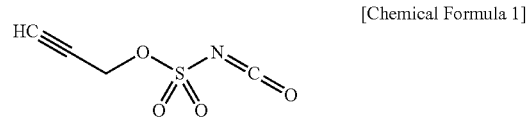

[Chemical Formula 1]

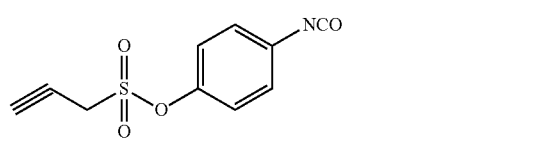

[Chemical Formula 2]

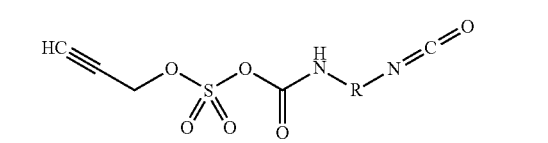

[Chemical Formula 3]

In Chemical Formula 3, R may be a linear or cyclic alkyl group, or an aromatic alkyl compound.

The isocyanate-based compound comprising a carbon-carbon triple bond may be comprised in 0.05% by weight to 2% by weight based on a total weight of the non-aqueous liquid electrolyte.

The lithium salt may comprise any one selected from the group consisting of $LiPF_6$, $LiAsF_6$, $LiCF_3SO_3$, $LiN(FSO_2)_2$, $LiN(CF_3SO_2)_2$, $LiBF_6$, $LiSbF_6$, $LiN(C_2F_5SO_2)_2$, $LiAlO_4$, $LiAlCl_4$, $LiSO_3CF_3$ and $LiClO_4$, or a mixture of two or more thereof, and the non-aqueous organic solvent may comprise a nitrile-based solvent, linear carbonate, cyclic carbonate, ester, ether, ketone or a combination thereof.

Advantageous Effects

A lithium secondary battery according to the present disclosure comprises an isocyanate-based compound comprising a carbon-carbon triple bond in a non-aqueous liquid electrolyte, and therefore, is capable of improving power output properties and stability of the produced secondary battery.

DESCRIPTION OF DRAWINGS

FIG. 1 is a graph showing results of measuring a degree of thickness increase after storing secondary batteries manufactured in Examples 1 to 4 and Comparative Example 1 at a high temperature.

MODE FOR CARRYING OUT THE INVENTION

Hereinafter, the present disclosure will be described in detail with reference embodiments. However, the embodiments according to the present disclosure may be modified to various other forms, and the scope of the present disclosure is not interpreted to be limited to the embodiments described below. The embodiments of the present disclosure are provided in order to more completely describe the present disclosure to those having average knowledge in the art.

A non-aqueous liquid electrolyte according to one embodiment of the present disclosure may comprise a non-aqueous organic solvent, a lithium salt, and an additive that is an isocyanate-based compound comprising a carbon-carbon triple bond.

The isocyanate-based compound readily reacts with an electrode surface in a thin film state, and is a compound having a structure favorably coordinating Li ions structurally, and specifically, the isocyanate-based compound may comprise one or more compounds selected from the group consisting of compounds represented by the following Chemical Formulae 1 to 3.

[Chemical Formula 1]

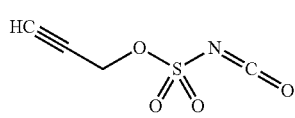

[Chemical Formula 2]

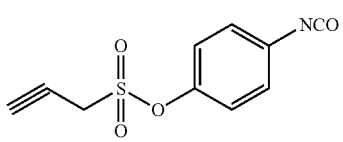

[Chemical Formula 3]

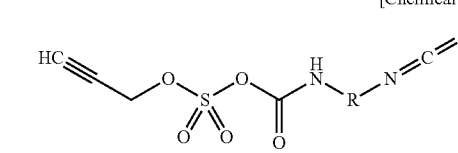

In Chemical Formula 3, R may be a linear or cyclic alkyl group, or an aromatic alkyl compound.

More specifically, R may be a hydrocarbon group excluding two isocyanate groups in one of compound selected from the group consisting of compounds represented by the following Chemical Formulae 4 to 7.

[Chemical Formula 4]

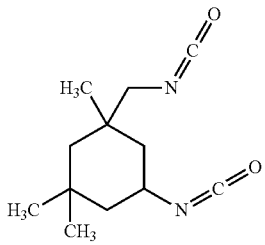

[Chemical Formula 5]

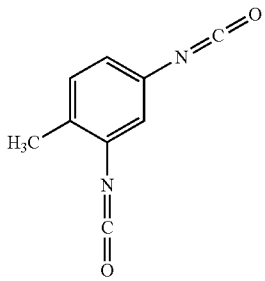

[Chemical Formula 6]

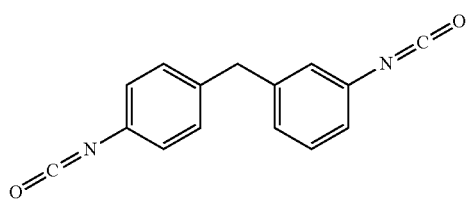

[Chemical Formula 7]

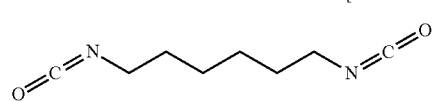

The additive according to one embodiment of the present disclosure has an affinity (-philic) with an —OH group on a positive electrode or negative electrode surface in a liquid electrolyte, and is capable of forming a uniform film. More specifically, + charge of the nitrogen (N) part in the isocyanate group of the isocyanate compound reacts with an —OH group on the positive electrode or negative electrode surface. Accordingly, the additive of the isocyanate-based compound according to one embodiment of the present disclosure is capable of forming a stable SEI film on the electrode surface.

Particularly, the carbon-carbon triple bond, one of functional groups in the isocyanate-based compound, is capable of forming a stable film through a reduction reaction, and a part having little reduction reaction is capable of forming a stable SEI film by reacting with an —OH group on the electrode surface through the isocyanate group. In other words, the compound comprising a carbon-carbon triple bond and an isocyanate group at the same time according to one embodiment of the present disclosure is capable more efficiently forming a film on the electrode surface through complementation.

Herein, the isocyanate-based compound additive may be comprised in 0.05% by weight to 2% by weight based on the total weight of the non-aqueous liquid electrolyte. When the content of the isocyanate-based compound is less than 0.05% by weight, effects of lifespan property enhancement and high temperature durability enhancement according to one embodiment of the present disclosure are low, and when the content is greater than 2% by weight, possibility of gas generation at high temperatures increases.

Moreover, the non-aqueous liquid electrolyte according to one embodiment of the present disclosure may further comprise a different type of additive. Particularly, the non-aqueous liquid electrolyte may further comprise a generally well-known additive for forming a solid electrolyte interface (SEI) depending on purposes. For example, an additive such as vinylene carbonate, vinyl ethylene carbonate, 1,3-propene sultone, 1,3-propane sultone, succinyl anhydride, lactam-based or caprolactam-based, which is a lifespan enhancing additive, may be further comprised in order to enhance a lifespan. In addition, for enhancing overcharge, cyclic hexyl benzene, biphenyl, para-chlorobenzene and the like may be further comprised. Such an additive is not limited to the above-mentioned examples, and various types of additives for forming negative electrode and positive electrode films may be further added to the electrolyte in order to enhance battery performance.

Examples of the lithium salt may comprise any one selected from the group consisting of $LiPF_6$, $LiAsF_6$, $LiCF_3SO_3$, $LiN(FSO_2)_2$, $LiN(CF_3SO_2)_2$, $LiBF_6$, $LiSbF_6$, $LiN(C_2F_5SO_2)_2$, $LiAlO_4$, $LiAlCl_4$, $LiSO_3CF_3$ and $LiClO_4$, or a mixture of two or more thereof.

The non-aqueous organic solvent that may be comprised in the non-aqueous liquid electrolyte is not limited as long as it minimizes decomposition by an oxidation reaction and the like during a charge and discharge process of a battery, and exhibits target properties with the additive, and examples thereof may comprise a nitrile-based solvent, cyclic carbonate, linear carbonate, ester, ether, ketone or the like. These may be used either alone or as a combination of two or more types.

The carbonate-based organic solvents may be useful among the organic solvents, and the cyclic carbonate may be any one selected from the group consisting of ethylene carbonate (EC), propylene carbonate (PC) and butylene carbonate (BC), or a mixture of two or more thereof, and the linear carbonate may be any one selected from the group consisting of dimethyl carbonate (DMC), diethyl carbonate (DEC), dipropyl carbonate (DPC), ethylmethyl carbonate (EMC), methylpropyl carbonate (MPC) and ethylpropyl carbonate (EPC), or a mixture of two or more thereof. The nitrile-based solvent may be one or more selected from the group consisting of acetonitrile, propionitrile, butyronitrile, valeronitrile, caprillonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile and 4-fluorophenylacetonitrile, and the non-aqueous solvent according to one embodiment of the present invention may use acetonitrile.

Another embodiment of the present disclosure may be a lithium secondary battery comprising a negative electrode, a positive electrode, a separator, and a non-aqueous liquid electrolyte comprising the isocyanate-based compound, wherein an SEI film is formed on a surface of at least any one of the negative electrode or the positive electrode.

The SEI film may be formed through an urethane bond or electrostatic interaction of a hydroxyl group (R'—OH) on the surface of the negative electrode or the positive electrode, and nitrogen (N) of an isocyanate-based compound of the non-aqueous liquid electrolyte, or formed through a reduction reaction of carbon-carbon triple bond, a functional group of the isocyanate-based compound while the isocyanate-based compound having a carbon-carbon triple bond comprised in the liquid electrolyte goes through an initial charge and discharge process or is injected to the liquid electrolyte in a secondary battery.

The positive electrode may be formed by applying a positive electrode mixture on a positive electrode collector and then drying the result, and the negative electrode may be formed by applying a negative electrode mixture on a negative electrode collector and then drying the result. Specifically, the positive electrode collector is not particularly limited as long as it has high conductivity without inducing chemical changes in the corresponding battery. For example, stainless steel, aluminum, nickel, titanium, baked carbon, or aluminum or stainless steel of which surface is treated with carbon, nickel, titanium, silver or the like, may be used. Herein, the positive electrode collector may use various forms such as films, sheets, foil, nets, porous bodies, foams and non-woven fabrics having fine unevenness formed on the surface so as to increase adhesive strength with the positive electrode active material.

In addition, the negative electrode collector is not particularly limited as long as it has conductivity without inducing chemical changes in the corresponding battery, and for example, copper, stainless steel, aluminum, nickel, titanium, baked carbon, or copper or stainless steel of which surface is treated with carbon, nickel, titanium, silver or the like, aluminum-cadmium alloys, or the like, may be used. Like the positive electrode collector, the negative electrode collector may use various forms such as films, sheets, foil, nets, porous bodies, foams and non-woven fabrics having fine unevenness formed on the surface. Furthermore, in the positive electrode or the negative electrode of the present disclosure, the positive electrode mixture or the negative electrode mixture may comprise an oxide containing at least one hydroxyl group (—OH) capable of being used in preparing a common positive electrode or negative electrode for a secondary battery.

Specifically, in the positive electrode mixture, the oxide may comprise any one lithium transition metal oxide selected from the group consisting of lithium cobalt-based oxides, lithium manganese-based oxides, lithium copper oxides, vanadium oxides, lithium nickel-based oxides, lithium manganese complex oxides and lithium-nickel-manganese-cobalt-based oxides, and more specifically, may comprise lithium manganese oxides such as $Li_{i+x}Mn_{2-x}O_4$ (herein, x is from 0 to 0.33), $LiMnO_3$, $LiMnO_2O_3$ and $LiMnO_2$; lithium copper oxides ($Li_2CuO_2$); vanadium oxides such as $LiV_3O_8$, $LiFe_3O_4$, $V_2O_5$ and $Cu_2V_2O_7$; lithium nickel oxides represented by $LiNi_{1-x}M_xO_2$ (herein, M=Co, Mn, Al, Cu, Fe, Mg, B or Ga, and x=0.01 to 0.3); lithium manganese complex oxides represented by $LiMn_{2-x}M_xO_2$ (herein, M=Co, Ni, Fe, Cr, Zn or Ta, and x=0.01 to 0.1) or $Li_2Mn_3MO_8$ (herein, M=Fe, Co, Ni, Cu or Zn), lithium-nickel-manganese-cobalt-based oxides represented by $Li(Ni_aCo_bMn_c)O_2$ (herein, 0<a<1, 0<b<1, 0<c<1, a+b+c=1), and the like, but is not limited thereto. In the negative electrode mixture, the oxide may comprise lithium-containing titanium complex oxides (LTO) facilitating lithium ion absorption and release, oxides (MeOx) of any one metal (Me) selected from the group consisting of Si, Sn, Li, Zn, Mg, Cd, Ce, Ni and Fe, or the like, and specifically, may comprise metal complex oxides such as $Li_xFe_2O_3$ (0=x=1), $Li_xWO_2$ (0<x=1), $Sn_xMe_{1-x}Me'_yO_z$ (Me:Mn, Fe, Pb, Ge; Me':Al, B, P, Si, elements of groups 1, 2 and 3 in the periodic table, halogen; 0<x=1; 1=y=3; 1=z=8); or oxides such as SnO, $SnO_2$, PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$ and $Bi_2O_5$, or the like, and carbon-based negative electrode active materials such as crystalline carbon, amorphous carbon or carbon complexes may be used either alone or as a mixture of two or more, and carbon powder may be used in one embodiment of the present disclosure.

Herein, the positive electrode mixture or the negative electrode mixture may further comprise a binder resin, a conductor, a filler and other additives.

The binder resin is a component assisting binding of the electrode active material and the conductor, and binding for the collector, and is normally added in 1% by weight to 50% by weight based on the total weight of the electrode mixture. Examples of such a binder may comprise polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene monomer (EPDM), a sulfonated-EPDM, styrene-butadiene rubber, fluorine rubber, various copolymers thereof and the like.

The conductor is a component for further enhancing conductivity of the electrode active material, and may be added in 1% by weight to 20% by weight based on the total weight of the electrode mixture. Such a conductor is not particularly limited as long as it has conductivity without inducing chemical changes in the corresponding battery, and examples thereof may comprise graphite such as natural graphite or artificial graphite; carbon black such as carbon black, acetylene black, Ketjen black, channel black, furnace black, lamp black or thermal black; conductive fiber such as carbon fiber or metal fiber; metal powder such as fluorocarbon, aluminum or nickel powder; conductive whiskers such as zinc oxide or potassium titanate; conductive metal oxides such as titanium oxide; polyphenylene derivatives, and the like.

The filler is a component suppressing expansion of the electrode, which may be used as necessary, and is not particularly limited as long as it is a fibrous material that does not induce chemical changes in the corresponding battery, and examples thereof may comprise olefin-based polymers such as polyethylene or polypropylene; or a fibrous material such as glass fiber or carbon fiber.

The separator may use common porous polymer films used as a separator in the art, and for example, porous polymer films prepared using polyolefin-based polymers such as an ethylene homopolymer, a propylene homopolymer, an ethylene/butene copolymer, an ethylene/hexene copolymer and an ethylene/methacrylate copolymer may be used either alone or as a laminate thereof, or common porous non-woven fabric, for example, non-woven fabric made of high melting point-glass fiber, polyethylene terephthalate fiber and the like, may be used, however, the separator is not limited thereto.

EXAMPLE

Example 1

(Preparation of Non-Aqueous Liquid Electrolyte)

A non-aqueous liquid electrolyte was prepared by adding a non-aqueous organic solvent having a composition of ethylene carbonate (EC): ethylmethyl carbonate (EMC): dimethyl carbonate (DMC)=3:3:4 (weight ratio), 1.0 mol/L of $LiPF_6$ based on the total amount of the non-aqueous liquid electrolyte as a lithium salt, and 0.5% by weight of a compound represented by Chemical Formula 1 based on the total amount of the non-aqueous liquid electrolyte as an additive.

(Preparation of Positive Electrode)

Positive electrode mixture slurry was prepared by adding 94% by weight of $Li(Ni_{0.6}Co_{0.2}Mn_{0.2})O_2$ as a positive electrode active material, 3% by weight of carbon black as a conductor and 3% by weight of PVdF as a binder to N-methyl-2-pyrrolidone (NMP), a solvent. The positive electrode mixture slurry was applied on an aluminum (Al) thin film, a positive electrode collector, having a thickness of 20 μm, and the result was dried to prepare a positive electrode comprising holes.

(Preparation of Negative Electrode)

Negative electrode mixture slurry was prepared by adding 95.5% by weight of carbon powder as a negative electrode active material, 1.5% by weight of Super-P (conductor) and 3% by weight of SBR/CMC (binder) to $H_2O$. This was coated on both surfaces of copper foil, and the result was dried and pressed to prepare a negative electrode.

(Battery Assembly)

The negative electrode and the positive electrode prepared as above, and a separator formed with three layers of polypropylene/polyethylene/polypropylene (PP/PE/PP) were assembled in a stacking manner, and then the liquid electrolyte prepared above was injected thereto to finally complete a battery.

Example 2

A secondary battery was completed in the same manner as in Example 1 except that an isocyanate-based compound formed with Chemical Formula 2 was used as the non-aqueous liquid electrolyte additive instead of the compound represented by Chemical Formula 1.

Example 3

A secondary battery was completed in the same manner as in Example 1 except that an isocyanate-based compound in which R is formed with Chemical Formula 4 in a compound of Chemical Formula 3 was used as the non-aqueous liquid electrolyte additive instead of the compound represented by Chemical Formula 1.

Example 4

A secondary battery was completed in the same manner as in Example 1 except that the compound represented by Chemical Formula 1 was used in 0.3% by weight and vinylene carbonate was used in 1% by weight as the non-aqueous liquid electrolyte additive.

Comparative Example 1

A secondary battery was completed in the same manner as in Example 1 except that the additive was not comprised in the non-aqueous liquid electrolyte.

Test Example 1

<Capacity Property Evaluation>

The secondary batteries manufactured in Examples 1 to 4 and Comparative Example 1 were charged up to 4.15 V/38 mA with 1 C under a constant current/constant voltage (CC/CV) condition, and then discharged down to 2.5 V with 1 C under a constant current (CC) condition, and the discharge capacity was measured. The results are shown in the following Table 1.

Test Example 2

<Discharge Resistance Measurement Using HPPC>

Resistance of the secondary batteries manufactured in Examples 1 to 4 and Comparative Example 1 was measured using a hybrid pulse power characterization (HPPC) test. The batteries were completely charged (SOC=100) up to 4.15 V with 1 C (30 mA), then discharged from SOC 100 to 10, and each of the batteries was stabilized for 1 hour. Discharge resistance of the each lithium secondary battery was measured in each SOC stage using a HPPC test method. The results are shown in the following Table 1.

Test Example 3

<Measurement on Battery Thickness Increase Rate>

Thicknesses of the secondary batteries manufactured in Examples 1 to 4 and Comparative Example 1 were measured, and the thicknesses were measured again after storing the batteries for one week and two weeks at 60° C. The degree of battery thicknesses is shown in FIG. 1.

TABLE 1

|  | Initial Capacity (mAh) | Discharge Resistance (mΩ) |
|---|---|---|
| Example 1 | 748 | 48 |
| Example 2 | 745 | 49 |
| Example 3 | 744 | 52 |
| Example 4 | 746 | 50 |
| Comparative Example 1 | 745 | 54 |

When referring to Table 1, it was identified that the lithium secondary batteries of Examples 1 to 4 comprising a non-aqueous liquid electrolyte that comprises the isocyanate-based compound comprising a carbon-carbon triple bond of the present disclosure as an additive exhibited lower discharge resistance compared to the lithium secondary battery of Comparative Example 1 that did not comprise the additive.

In addition, when referring to FIG. 1, the lithium secondary batteries of Examples 1 to 4 comprising a non-aqueous liquid electrolyte that comprises the isocyanate-based compound comprising a carbon-carbon triple bond of the present disclosure as an additive experienced a small thickness increase when stored at a high temperature, and particularly, the differences in the thickness increase were more significant when two weeks had passed after the batteries were stored at a high temperature, and it can be identified that a lithium secondary battery is capable of having enhanced high temperature storability and thereby reducing a thickness increase after high temperature storage when comprising the isocyanate-based compound comprising a carbon-carbon triple bond as an additive.

What is claimed is:

1. A non-aqueous liquid electrolyte comprising a non-aqueous organic solvent, a lithium salt and an additive, wherein the additive comprises at least one isocyanate-based compound comprising a carbon-carbon triple bond, selected from the group consisting of compounds represented by the following Chemical Formulae 1 to 3:

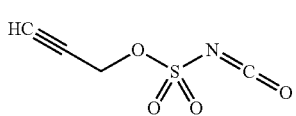
[Chemical Formula 1]

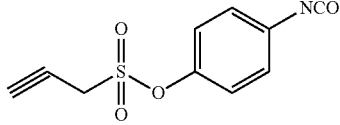
[Chemical Formula 2]

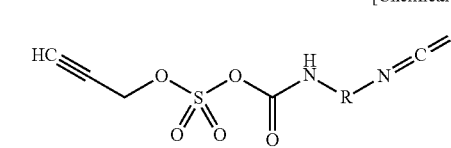
[Chemical Formula 3]

wherein, in Chemical Formula 3, R is a linear or cyclic alkyl group, or an aromatic alkyl compound.

2. The non-aqueous liquid electrolyte of claim 1, wherein R of the compound represented by Chemical Formula 3 is a hydrocarbon group excluding two isocyanate groups in one of compound selected from the group consisting of compounds represented by the following Chemical Formulae 4 to 7:

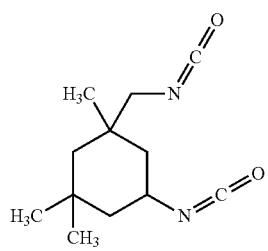
[Chemical Formula 4]

[Chemical Formula 5]

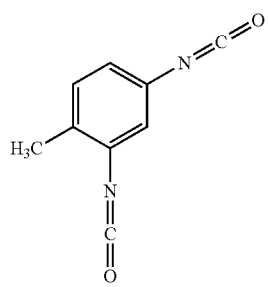
[Chemical Formula 6]

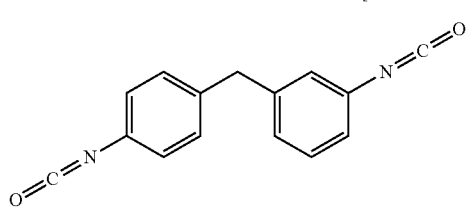
[Chemical Formula 7]

3. The non-aqueous liquid electrolyte of claim 1, wherein the lithium salt comprises any one selected from the group consisting of LiPF$_6$, LiAsF$_6$, LiCF$_3$SO$_3$, LiN(FSO$_2$)$_2$, LiN(CF$_3$SO$_2$)$_2$, LiBF$_6$, LiSbF$_6$, LiN(C$_2$F$_5$SO$_2$)$_2$, LiAlO$_4$, LiAlCl$_4$, LiSO$_3$CF$_3$ and LiClO$_4$, or a mixture of two or more thereof.

4. The non-aqueous liquid electrolyte of claim 1, wherein the non-aqueous organic solvent comprises a nitrile-based solvent, linear carbonate, cyclic carbonate, ester, ether, ketone, or a combination thereof.

5. The non-aqueous liquid electrolyte of claim 4, wherein the cyclic carbonate is any one selected from the group consisting of ethylene carbonate (EC), propylene carbonate (PC) and butylene carbonate (BC), or a mixture of two or more thereof, and the linear carbonate is any one selected from the group consisting of dimethyl carbonate (DMC), diethyl carbonate (DEC), dipropyl carbonate (DPC), ethylmethyl carbonate (EMC), methylpropyl carbonate (MPC) and ethylpropyl carbonate (EPC), or a mixture of two or more thereof.

6. The non-aqueous liquid electrolyte of claim 4, wherein the nitrile-based solvent is one or more selected from the group consisting of acetonitrile, propionitrile, butyronitrile, valeronitrile, caprillonitrile, heptanenitrile, cyclopentane carbonitrile, cyclohexane carbonitrile, 2-fluorobenzonitrile, 4-fluorobenzonitrile, difluorobenzonitrile, trifluorobenzonitrile, phenylacetonitrile, 2-fluorophenylacetonitrile and 4-fluorophenylacetonitrile.

7. The non-aqueous liquid electrolyte of claim 1, wherein the isocyanate-based compound comprising a carbon-carbon triple bond is comprised in 0.05% by weight to 2% by weight based on a total weight of the non-aqueous liquid electrolyte.

8. A lithium secondary battery comprising a negative electrode, a positive electrode, a separator and a non-aqueous liquid electrolyte,
wherein the non-aqueous liquid electrolyte is the non-aqueous liquid electrolyte of claim 1 and
an SEI film is formed on a surface of at least any one of the negative electrode or the positive electrode.

9. The lithium secondary battery of claim 8, wherein the SEI film is formed through an urethane bond or electrostatic interaction of a hydroxyl group (R'—OH) on the surface of the negative electrode or the positive electrode, and nitrogen (N) of the isocyanate-based compound comprising a carbon-carbon triple bond of the non-aqueous liquid electrolyte, or formed through a reduction reaction of the carbon-carbon triple bond, a functional group of the isocyanate-based compound.

10. A lithium secondary battery comprising a negative electrode, a positive electrode, a separator and a non-aqueous liquid electrolyte,
wherein the non-aqueous liquid electrolyte is the non-aqueous liquid electrolyte of claim 1, and
an SEI film is formed on a surface of at least any one of the negative electrode or the positive electrode.

11. A lithium secondary battery comprising a negative electrode, a positive electrode, a separator and a non-aqueous liquid electrolyte,
wherein the non-aqueous liquid electrolyte is the non-aqueous liquid electrolyte of claim 2, and
an SEI film is formed on a surface of at least any one of the negative electrode or the positive electrode.

12. A lithium secondary battery comprising a negative electrode, a positive electrode, a separator and a non-aqueous liquid electrolyte,
wherein the non-aqueous liquid electrolyte is the non-aqueous liquid electrolyte of claim 3, and
an SEI film is formed on a surface of at least any one of the negative electrode or the positive electrode.

13. A lithium secondary battery comprising a negative electrode, a positive electrode, a separator and a non-aqueous liquid electrolyte,
wherein the non-aqueous liquid electrolyte is the non-aqueous liquid electrolyte of claim 4, and
an SEI film is formed on a surface of at least any one of the negative electrode or the positive electrode.

14. A lithium secondary battery comprising a negative electrode, a positive electrode, a separator and a non-aqueous liquid electrolyte,
wherein the non-aqueous liquid electrolyte is the non-aqueous liquid electrolyte of claim 6, and
an SEI film is formed on a surface of at least any one of the negative electrode or the positive electrode.

15. A lithium secondary battery comprising a negative electrode, a positive electrode, a separator and a non-aqueous liquid electrolyte,
wherein the non-aqueous liquid electrolyte is the non-aqueous liquid electrolyte of claim 6, and
an SEI film is formed on a surface of at least any one of the negative electrode or the positive electrode.

16. A lithium secondary battery comprising a negative electrode, a positive electrode, a separator and a non-aqueous liquid electrolyte,
wherein the non-aqueous liquid electrolyte is the non-aqueous liquid electrolyte of claim 7, and
an SEI film is formed on a surface of at least any one of the negative electrode or the positive electrode.

* * * * *